US007835495B2

(12) United States Patent
Harding

(10) Patent No.: US 7,835,495 B2
(45) Date of Patent: Nov. 16, 2010

(54) SYSTEM AND METHOD FOR X-RAY DIFFRACTION IMAGING

(75) Inventor: Geoffrey Harding, Hamburg (DE)

(73) Assignee: Morpho Detection, Inc., Newark, CA (US)

( * ) Notice: Subject to any disclaimer, the term of this patent is extended or adjusted under 35 U.S.C. 154(b) by 7 days.

(21) Appl. No.: 12/263,023

(22) Filed: Oct. 31, 2008

(65) Prior Publication Data

US 2010/0111255 A1 May 6, 2010

(51) Int. Cl.
  *G01N 23/20* (2006.01)
  *G01N 23/083* (2006.01)
(52) U.S. Cl. .............................. 378/87; 378/6; 378/57; 378/71; 378/86
(58) Field of Classification Search ...................... 378/6, 378/57, 71, 73, 86–90
  See application file for complete search history.

(56) References Cited

U.S. PATENT DOCUMENTS

| 4,236,356 | A | | 12/1980 | Ward |
| 4,672,648 | A | | 6/1987 | Mattson et al. |
| 4,679,973 | A | | 7/1987 | Kodama et al. |
| 4,787,147 | A | | 11/1988 | Wiley |
| 4,963,746 | A | | 10/1990 | Morgan et al. |
| 5,428,657 | A | * | 6/1995 | Papanicolopoulos et al. .. 378/86 |
| 5,600,303 | A | | 2/1997 | Husseiny et al. |
| 5,600,700 | A | * | 2/1997 | Krug et al. ..................... 378/57 |
| 5,682,412 | A | | 10/1997 | Skillicorn et al. |
| 5,692,029 | A | | 11/1997 | Husseiny et al. |
| 5,859,893 | A | | 1/1999 | Moorman et al. |
| 6,054,712 | A | * | 4/2000 | Komardin et al. ...... 250/363.06 |
| 6,192,104 | B1 | * | 2/2001 | Adams et al. .................. 378/90 |
| 6,269,142 | B1 | * | 7/2001 | Smith ........................... 378/57 |
| 6,269,144 | B1 | | 7/2001 | Dube et al. |
| 6,442,233 | B1 | * | 8/2002 | Grodzins et al. .............. 378/57 |
| 6,684,676 | B2 | | 2/2004 | Oumi et al. |
| 6,807,248 | B2 | | 10/2004 | Mihara et al. |
| 6,816,564 | B2 | | 11/2004 | Charles, Jr. et al. |
| 6,839,406 | B2 | | 1/2005 | Ries et al. |
| 6,917,396 | B2 | | 7/2005 | Hiraishi et al. |

(Continued)

FOREIGN PATENT DOCUMENTS

WO  2005102170 A1  11/2005

(Continued)

OTHER PUBLICATIONS

PCT, International Search Report, PCT US2007/074933 dated Mar. 12, 2008, 6 pages.

(Continued)

*Primary Examiner*—Edward J Glick
*Assistant Examiner*—Thomas R Artman
(74) *Attorney, Agent, or Firm*—Armstrong Teasdale LLP

(57) ABSTRACT

An X-ray diffraction imaging system is provided. The X-ray diffraction imaging system includes an X-ray source configured to emit an X-ray pencil beam and a scatter detector configured to receive scattered radiation having a scatter angle from the X-ray pencil beam. The scatter detector is located substantially in a plane and includes a plurality of detector strips. A first detector strip has a first width equal to a linear extent of the X-ray pencil beam measured at the plane in a direction parallel to the first width.

18 Claims, 7 Drawing Sheets

U.S. PATENT DOCUMENTS

| | | | |
|---|---|---|---|
| 6,975,752 | B2 | 12/2005 | Dixon et al. |
| 7,065,175 | B2 | 6/2006 | Green |
| 7,092,485 | B2 * | 8/2006 | Kravis .................. 378/57 |
| 7,274,768 | B2 | 9/2007 | Green |
| 7,283,613 | B2 | 10/2007 | Harding |
| 7,365,536 | B2 | 4/2008 | Crowley et al. |
| 7,555,099 | B2 * | 6/2009 | Rothschild et al. ............ 378/90 |
| 2001/0033636 | A1 | 10/2001 | Hartick et al. |
| 2004/0222790 | A1 | 11/2004 | Karmi et al. |
| 2005/0281383 | A1 | 12/2005 | Harding et al. |
| 2007/0133749 | A1 | 6/2007 | Mazin et al. |
| 2007/0158573 | A1 | 7/2007 | Deych |
| 2007/0284533 | A1 | 12/2007 | Green |
| 2008/0031415 | A1 | 2/2008 | Harding |

FOREIGN PATENT DOCUMENTS

WO          2007068933 A1     6/2007

OTHER PUBLICATIONS

Business Wire, Quantum Magnetics, i-Portal 100, Nov. 1, 2001, 2 pages.

Robert E. Alvarez and Albert Macovski, Energy-Selective Reconstructions in X-Ray Computerized Tomography, Department of Electrical Engineering, Standford University, Phys. Med. Biol., 1976, 12 pages, vol. 21, No. 5, 733-744.

J. H. Hubbell, et al., Atomic Form Factors, Incoherent Scattering Functions, and Photon Scattering Cross Sections, J. Phys. Chem Ref. Data, 1975, 68 pages, vol. 4, No. 3.

J. H. Hubbell, et al., Erratum: Atomic Form Factors, Incoherent Scattering Functions, and Photon Scattering Cross Sections, J. Phys. Chem Ref. Data, 1977, 2 pages, vol. 6, No. 2.

Jens-Peter Schlomka, et al., Coherent Scatter Computed Tomography—A Novel Medical Imaging Technique, Medical Imaging 2003: Physics of Medical Imaging, 2003, 10 pages, SPIE vol. 5030.

Rabiej, Malgorzata, Determination of the Degree of Crystallinity of Semicrystalline Polymers by Means of the "OptiFit" Computer Software, Polimery, 2002, 5 pages, 423-427, 47, nr 6.

Kratos Analytical, XRD-6000 Application Brief: Percentage Crystallinity Determination by X-Ray Diffraction, 6 pages.

A. M. Hindeleh and D. J. Johnson, The Resolution of Multipeak Data in Fibre Science, J. Phys. D: Appl. Phys., 1971, 5 pages, vol. 4.

Patent Cooperation Treaty, The International Search Report and Written Opinion of the International Searching Authority, PCT/US2009/062547, Jun. 23, 2010, 116 pages.

* cited by examiner

SYSTEM AND METHOD FOR X-RAY DIFFRACTION IMAGING

FIELD OF THE INVENTION

The embodiments described herein relate generally to X-ray diffraction imaging and, more particularly, to the use of combined multiview transmission imaging and X-ray diffraction imaging in security detection systems.

BACKGROUND OF THE INVENTION

Known security detection systems are used at travel checkpoints to inspect carry-on and/or checked bags for concealed weapons, narcotics, and/or explosives. At least some known security detection systems include X-ray imaging systems. In an X-ray imaging system, an X-ray source transmits X-rays through a container, for example a suitcase, towards a detector, and the detector output is processed to identify a set of objects and/or materials in the container.

At least some known security detection systems utilize "Advanced Technology" (AT) scanners for multiview transmission imaging. Such known security detection systems view a container from two or three X-ray source perspectives. The resulting projection images may be compared to model projection images of hypothetical container contents, such as clothes, hygiene articles, books, or other common objects, to allow objects in the container to be recognized. In at least some known security detection systems, the multiview projections also may be combined using tomosynthesis or "limited angle reconstruction" to derive section images of the container. The use of each, or a combination, of these techniques for processing stereoscopic information provides enhanced detection of threats relative to single perspective X-ray screening machines. However, an amount of information about the contents of a container that can be derived from multiview transmission imaging using only two or three X-ray source perspectives is disadvantageously limited.

In addition, at least some known security detection systems include X-ray diffraction imaging (XDI) systems. At least some known XDI systems use inverse fan-beam geometry (a large source and a small detector) and a multi-focus X-ray source (MFXS). At least some known XDI systems provide an improved discrimination of materials, as compared to that provided by other known X-ray imaging systems, by measuring d-spacings between lattice planes of micro-crystals in materials. It is also known that X-ray diffraction may yield data from a molecular interference function that may be used to identify other materials, such as liquids, in a container. However, at least some known XDI systems generate an increased number of false positives due to a relatively low number of photons received at a detector element from a voxel of the container being scanned. In addition, while a number of photons received at a detector element may be increased by increasing an angular broadening of a scatter angle associated with the detector, such increased angular broadening results in an X-ray diffraction profile with increased measured peak widths of momentum transfer. Because narrower peak widths facilitate an identification of a scanned material, a disadvantageous result of angular broadening of the scatter angle to increase a number of photons received at a detector element is a corresponding decreased detection rate of a material.

To obtain the advantages of both multiview transmission imaging and XDI, at least some known security detection systems implement separate AT and XDI scanning systems. This increases both a size and a cost of the security detection system, and also increases a time needed to complete an investigation of each container.

BRIEF DESCRIPTION OF THE INVENTION

In one aspect, an X-ray diffraction imaging system is provided. The X-ray diffraction imaging system includes an X-ray source configured to emit an X-ray fan beam and a set of X-ray pencil beams. The X-ray diffraction imaging system also includes an examination area, a plurality of scatter detectors each configured to receive scattered radiation from an interaction of an X-ray pencil beam and a container in the examination area, and a transmission detector array configured to receive the X-ray fan beam attenuated by the container. The received scattered radiation has a scatter angle. At least one of the plurality of scatter detectors is located substantially in a plane and comprises a plurality of detector strips. A first detector strip of the plurality of detector strips has a first width equal to a linear extent of the X-ray pencil beam measured at the plane in a direction parallel to the first width. The X-ray diffraction imaging system further includes a data processing system configured to combine an output from the transmission detector array and an output from the plurality of scatter detectors to generate information regarding the container.

In another aspect, a method of operating an X-ray diffraction imaging system is provided. The method includes receiving at a plurality of scatter detectors a portion of scattered radiation from a container. The scattered radiation has a scatter angle. At least one of the plurality of scatter detectors is located substantially in a plane and comprises a plurality of detector strips. A first width of a first detector strip of the plurality of detector strips is equal to a linear extent of an X-ray pencil beam measured at the plane in a direction parallel to the first width. The method also includes receiving an X-ray fan beam attenuated by the container at a transmission detector array. The method further includes generating information regarding the contents of the container by combining an output from the transmission detector array and an output from the plurality of scatter detectors.

In still another aspect, an X-ray scatter detection system is provided. The X-ray scatter detection system includes an X-ray source configured to emit an X-ray pencil beam and a scatter detector configured to receive scattered radiation having a scatter angle from the X-ray pencil beam. The scatter detector is located substantially in a plane and includes a plurality of detector strips. A first detector strip has a first width equal to a linear extent of the X-ray pencil beam measured at the plane in a direction parallel to the first width.

BRIEF DESCRIPTION OF THE DRAWINGS

FIG. 1 is a schematic view, in an X-Z plane, of an exemplary embodiment of a security detection system.

FIG. 2 is a schematic view, in an X-Y plane, of an exemplary embodiment of the security detection system shown in FIG. 1.

FIG. 3 is a schematic view, in an X-Z plane, of an exemplary embodiment an X-ray scatter detection system embodied within the security detection system shown in FIGS. 1 and 2.

FIG. 4 illustrates an angular broadening of a scatter angle of scattered radiation originating from a representative object voxel in an exemplary embodiment.

FIG. 5 shows an X-Y plane projection of an optimal geometric relationship for a detector strip in an exemplary embodiment.

FIG. 6 is a schematic view, in a Y-Z plane as seen from an X-ray source, of the geometry of a scatter detector in an exemplary embodiment.

FIG. 7 is a flowchart of an exemplary method for operating the security detection system as shown in FIGS. 1 and 2.

DETAILED DESCRIPTION OF THE INVENTION

While described in terms of detecting contraband including, without limitation, weapons, explosives, and/or narcotics, within checked or carry-on baggage, the embodiments described herein can be used for any suitable security detection or other X-ray diffraction imaging application, including applications in the plastics recycling, pharmaceutical and non-destructive testing industries. Furthermore, the term "parallel" as used herein refers to planes, lines, curves, and/or layers that are equidistantly spaced apart and never intersect each other. Moreover, angles and dimensions shown in the accompanying figures herein are not to scale, and may be exaggerated for clarity.

Figure 1:
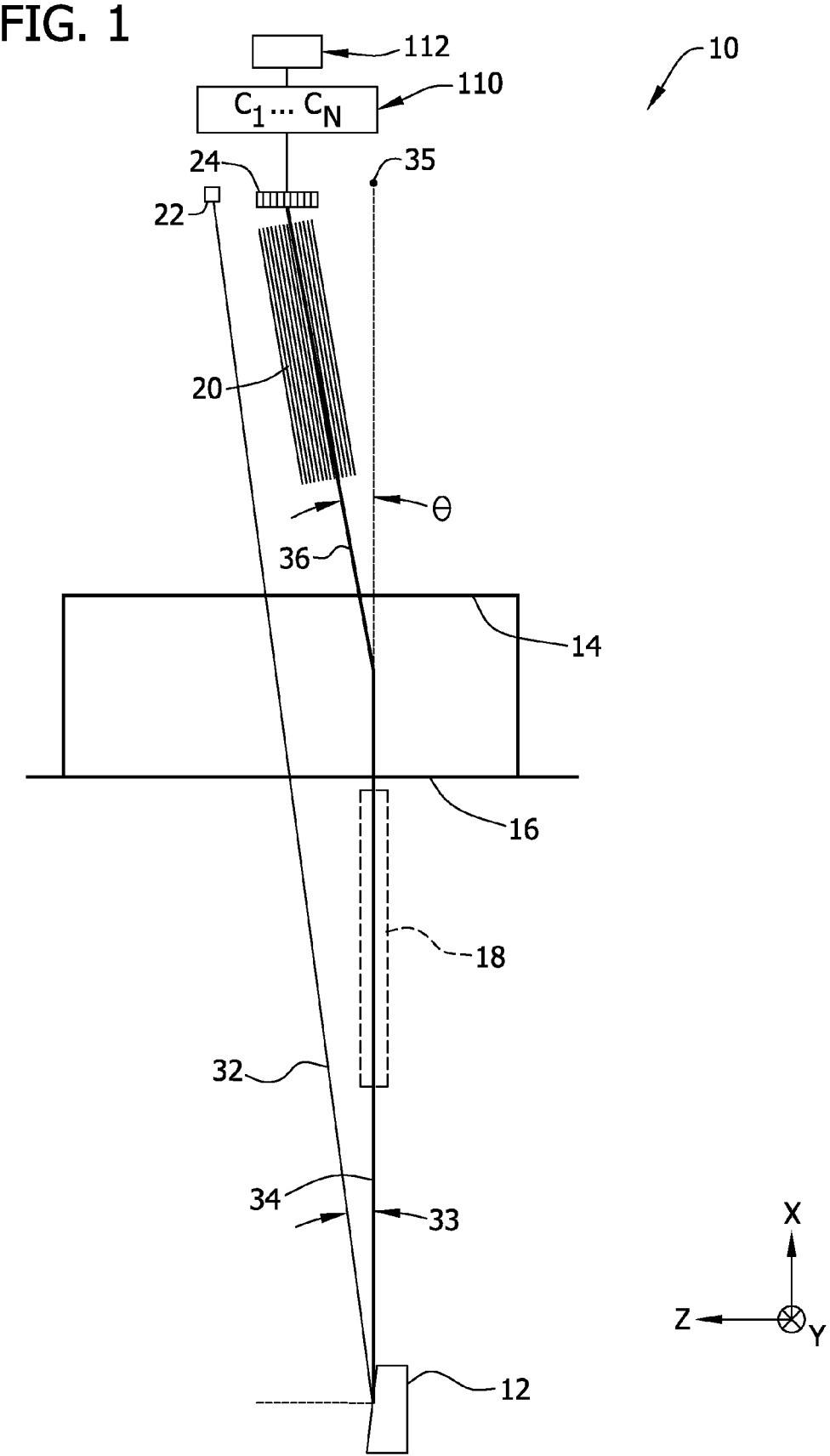
FIGS. 1-7 show exemplary embodiments of the systems and method described herein.

FIG. 1 is a schematic view, in an X-Z plane, of an exemplary embodiment of a security detection system 10. In the exemplary embodiment, security detection system 10 includes an X-ray source 12, an examination area 14, a support surface 16, a primary collimator 18, and a secondary collimator 20. System 10 also includes two types of detectors, a transmission detector array 22 and a plurality 24 of discrete coherent X-ray scatter detectors. Transmission detector array 22 is offset in the Z-axis direction from the plurality 24 of scatter detectors.

In the exemplary embodiment, X-ray source 12 is a multi-focus X-ray source (MFXS) capable of emitting X-ray radiation sequentially from a plurality of focus points distributed along the MFXS in a direction substantially parallel to the Y-axis. In the exemplary embodiment, the MFXS has approximately 40 focus points. In an alternative embodiment, the MFXS has approximately 100 focus points. In further alternative embodiments, the MFXS has any suitable number of focus points that will allow security detection system 10 to function as herein described.

Furthermore, in the exemplary embodiment, X-ray source 12 is located on a lower support surface, such as a floor, while transmission detector array 22 and the plurality 24 of scatter detectors are located on an upper support structure, such as a ceiling. In an alternative embodiment, X-ray source is located on an upper support structure, such as a ceiling, while transmission detector array 22 and the plurality 24 of scatter detectors are located on a lower support surface, such as a floor. Furthermore, in the exemplary embodiment, X-ray source 12, transmission detector array 22 and the plurality 24 of scatter detectors are stationary, support 16 is a conveyor belt capable of movement backward and forward in a direction substantially parallel to the Z-axis, and examination area 14 is a baggage tunnel through which the conveyor belt moves. In an alternative embodiment, X-ray source 12, transmission detector array 22 and the plurality 24 of scatter detectors are capable of coordinated movement at least in a direction substantially parallel to the Z-axis, and support 16 is stationary. In certain alternative embodiments, X-ray source 12, transmission detector array 22, the plurality 24 of scatter detectors and support 16 are all capable of movement.

In the exemplary embodiment, X-ray source 12 is capable of emitting an X-ray fan beam 32 from each focus point of X-ray source 12. Each fan beam 32 lies substantially in a plane at an angle 33 relative to the vertical X-axis. Each fan beam 32 is directed at transmission detector array 22. In the exemplary embodiment, angle 33 is approximately ten degrees. In an alternative embodiment, angle 33 is approximately fifteen degrees. In further alternative embodiments, angle 33 is any suitable angle that will allow security detection system 10 to function as herein described.

In addition, X-ray source 12 is capable of emitting, through primary collimator 18, a set 34 of X-ray pencil beams from each focus point of X-ray source 12. Each pencil beam of the set 34 of pencil beams is directed at a corresponding target point of a plurality 35 of target points which lie in the same X-Y plane as the X-ray source 12. Furthermore, each of the plurality 35 of target points is positioned at the same X coordinate, but at different Y values. Because each pencil beam of the set 34 of pencil beams is emitted in the same X-Y plane, only one pencil beam of the set 34 (and only one of the plurality 35 of target points) is visible in the X-Z cross-section view of FIG. 1.

A portion of the X-ray radiation from each pencil beam of the set 34 of pencil beams typically is scattered in various directions upon contact with a container (not shown) in examination area 14. Secondary collimator 20 is configured to facilitate ensuring that a portion of scattered radiation 36 arriving at each of the plurality 24 of scatter detectors has a constant scatter angle θ with respect to the corresponding pencil beam of the set 34 of X-ray pencil beams from which the scattered radiation 36 originated. In certain embodiments, scatter angle θ is approximately 0.04 radians. The plurality 24 of scatter detectors can be positioned between the set 34 of X-ray pencil beams and the fan beam 32 to ensure that only scattered radiation from the former and not the latter is detected. For example, secondary collimator 20 is configured to absorb scattered radiation (not shown) that is not parallel to the direction of the scattered radiation 36. Furthermore, although, in the exemplary embodiment, secondary collimator 20 and the plurality 24 of scatter detectors are positioned on one side of the set 34 of pencil beams with respect to the Z-axis, in alternative embodiments secondary collimator 20 and the plurality 24 of scatter detectors may be positioned on the other side, or on both sides, of the set 34 of pencil beams with respect to the Z-axis.

In the exemplary embodiment, the detectors in transmission detector array 22 include charge integration detectors, while the plurality 24 of scatter detectors includes pulse-counting energy-resolving detectors. Transmission detector array 22 and each of the plurality 24 of scatter detectors are in electronic communication with a number of channels 110, for example, N number of channels $C_1, \ldots, C_N$, wherein N is selected based on the configuration of security detection system 10. Channels 110 electronically communicate data collected by transmission detector array 22 and each of the plurality 24 of scatter detectors to data processing system 112. In the exemplary embodiment, data processing system 112 combines an output from transmission detector array 22 and an output from the plurality 24 of scatter detectors to generate information about the contents of examination area 14. For example, but not by way of limitation, data processing system 112 may generate multiview projections and/or section images of a container (not shown) in examination area 14 that identify a location in the container of specific materials detected by XDI analysis.

Figure 2:
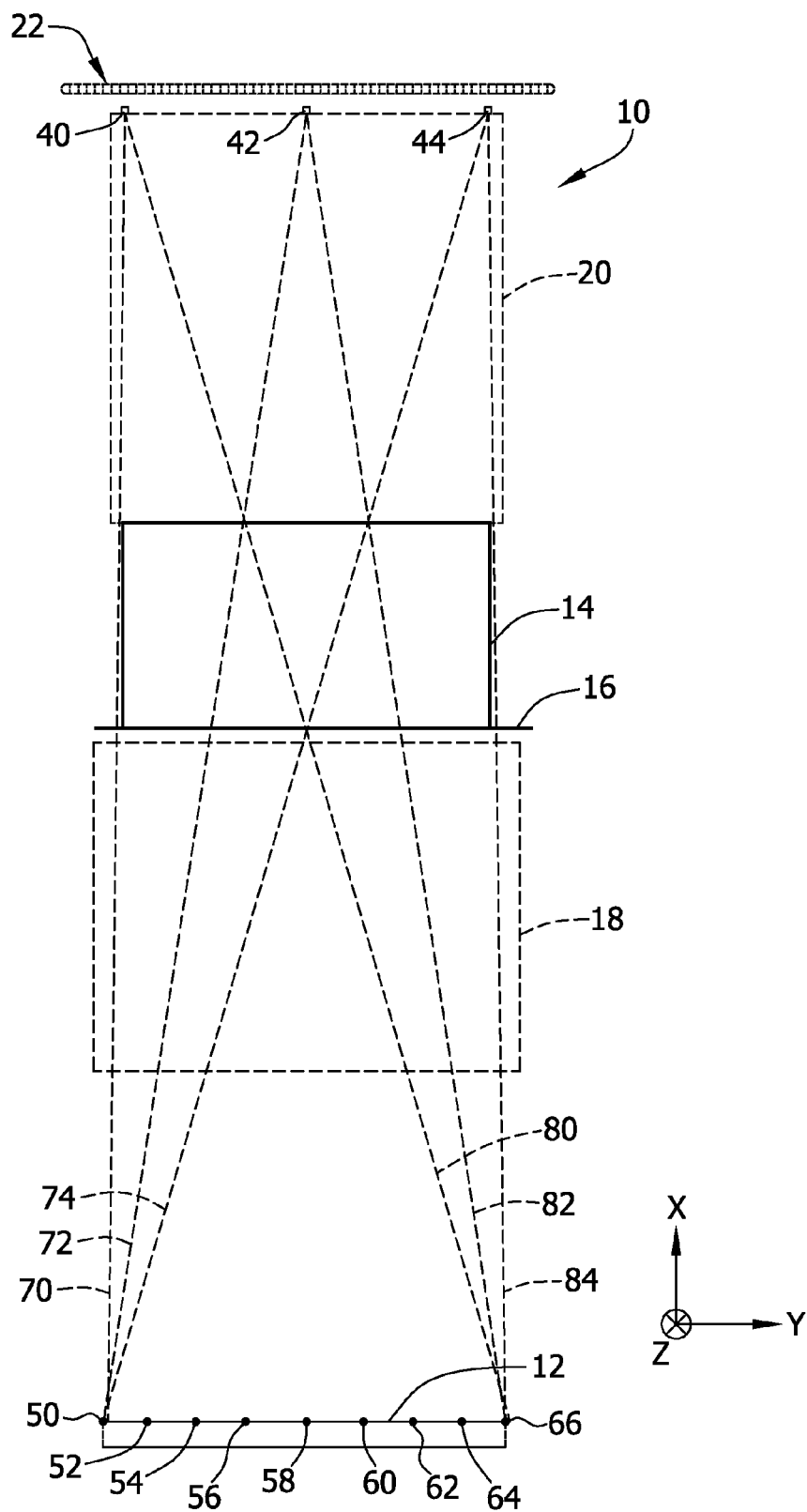

FIG. 2 is a schematic view, in an X-Y plane, of an exemplary embodiment of security detection system 10 shown in FIG. 1. With reference to FIGS. 1 and 2, in the exemplary embodiment, the plurality 24 of scatter detectors includes three discrete coherent X-ray scatter detectors 40, 42 and 44.

Scatter detectors 40, 42 and 44 share identical X and Z coordinates and are spaced apart in a direction substantially parallel to the Y-axis. Moreover, in the exemplary embodiment, each set 34 of pencil beams generated by X-ray source 12 includes three pencil beams corresponding to the number (three) of scatter detectors 40, 42 and 44. In alternative embodiments, a different number of scatter detectors and corresponding different number of pencil beams in the set 34 of pencil beams may be used.

As previously described, X-ray source 12 includes a plurality of focus points, of which focus points 50, 52, 54, 56, 58, 60, 62, 64 and 66 are shown in FIG. 2. X-ray source 12 is capable of sequentially generating both a fan beam 32 and, through primary collimator 18, a set 34 of pencil beams from each focus point such as focus point 50, 52, 54, 56, 58, 60, 62, 64 and 66. Each pencil beam of each set 34 of pencil beams is targeted at a target point 35 associated with one of scatter detectors 40, 42 and 44. For example, the set 34 of pencil beams generated from focus point 50 includes pencil beam 70, pencil beam 72 and pencil beam 74, and scattered radiation 36 at angle θ (shown in FIG. 1) from pencil beam 70 is received by discrete coherent X-ray detector 40, scattered radiation 36 from pencil beam 72 is received by discrete coherent X-ray detector 42, and scattered radiation 36 from pencil beam 74 is received by discrete coherent X-ray detector 44 respectively. For another example, the set 34 of pencil beams generated from focus point 66 includes pencil beam 80, pencil beam 82 and pencil beam 84, and scattered radiation 36 at angle θ from pencil beam 80 is received by discrete coherent X-ray detector 40, scattered radiation 36 from pencil beam 82 is received by discrete coherent X-ray detector 42, and scattered radiation 36 from pencil beam 84 is received by discrete coherent X-ray detector 44, respectively.

In addition, each fan beam 32 generated sequentially from each focus point of X-ray source 12, such as focus point 50, 52, 54, 56, 58, 60, 62, 64 and 66, is targeted at transmission detector array 22. Transmission detector array 22 extends in a direction substantially parallel to the Y-axis. Transmission detector array 22 typically receives radiation from each fan beam 32 after it is attenuated by a container (not shown) in examination area 14. In the exemplary embodiment, transmission detector array 22 is a dual energy transmission detector array. In certain embodiments, transmission detector array 22 includes approximately 1000 detector elements.

In the exemplary embodiment, security detection system 10 is configured to operate such that focus point 50, the focus point at a first end of X-ray source 12 relative to the Y-direction, first simultaneously generates both a fan beam 32 and set 34 of pencil beams for which data is collected from transmission detector array 22 and scatter detectors 40, 42 and 44, respectively, and electronically communicated to data processing system 112. Then, focus point 52, the focus point of X-ray source 12 adjacent focus point 50 in the Y-direction, simultaneously generates both a fan beam 32 and set 34 of pencil beams for which data is collected from transmission detector array 22 and scatter detectors 40, 42 and 44, respectively, and electronically communicated to data processing system 112. The remaining focus points 54, 56, 58, 60, 62, 64 and 66, in sequence along the Y-direction, likewise simultaneously generate both fan beam 32 and set 34 of pencil beams for which data is collected from transmission detector array 22 and scatter detectors 40, 42 and 44, respectively, and electronically communicated to data processing system 112. Security detection system 10 then repeats the sequence starting with focus point 50 again. In certain embodiments, the container under examination (not shown) moves in the Z-direction relative to X-ray source 12 at a speed that is relatively slow compared to a speed at which X-ray source 12 switches among focus points.

In alternative embodiments, each focus point generates fan beam 32 and set 34 of pencil beams in non-simultaneous fashion. Moreover, in alternative embodiments, the focus points of X-ray source 12 generate fan beam 32 and set 34 of pencil beams in a sequence that is not based upon their relative position along the Y-direction. In an exemplary embodiment for checkpoint or "carry-on" luggage screening, transmission detector array 22 has a length parallel to the Y-axis of approximately 650 mm, the plurality 24 of scatter detectors is spaced sequentially at approximately 250 mm intervals in a direction substantially parallel to the Y-axis, and transmission detector array 22 and the plurality 24 of scatter detectors are each located approximately 1500 mm apart from X-ray source 12 in a direction substantially parallel to the X-axis. In an exemplary embodiment for checked luggage screening, transmission detector array 22 has a length parallel to the Y-axis of approximately 2000 mm, the plurality 24 of scatter detectors is spaced sequentially at approximately 50 mm intervals in a direction substantially parallel to the Y-axis, and transmission detector array 22 and the plurality 24 of scatter detectors are each located approximately 2000 mm apart from X-ray source 12 in a direction substantially parallel to the X-axis. In alternative embodiments, other suitable dimensions are used that allow all desired portions of examination area 14 to be covered for both XDI analysis and multiview transmission imaging.

Figure 3:
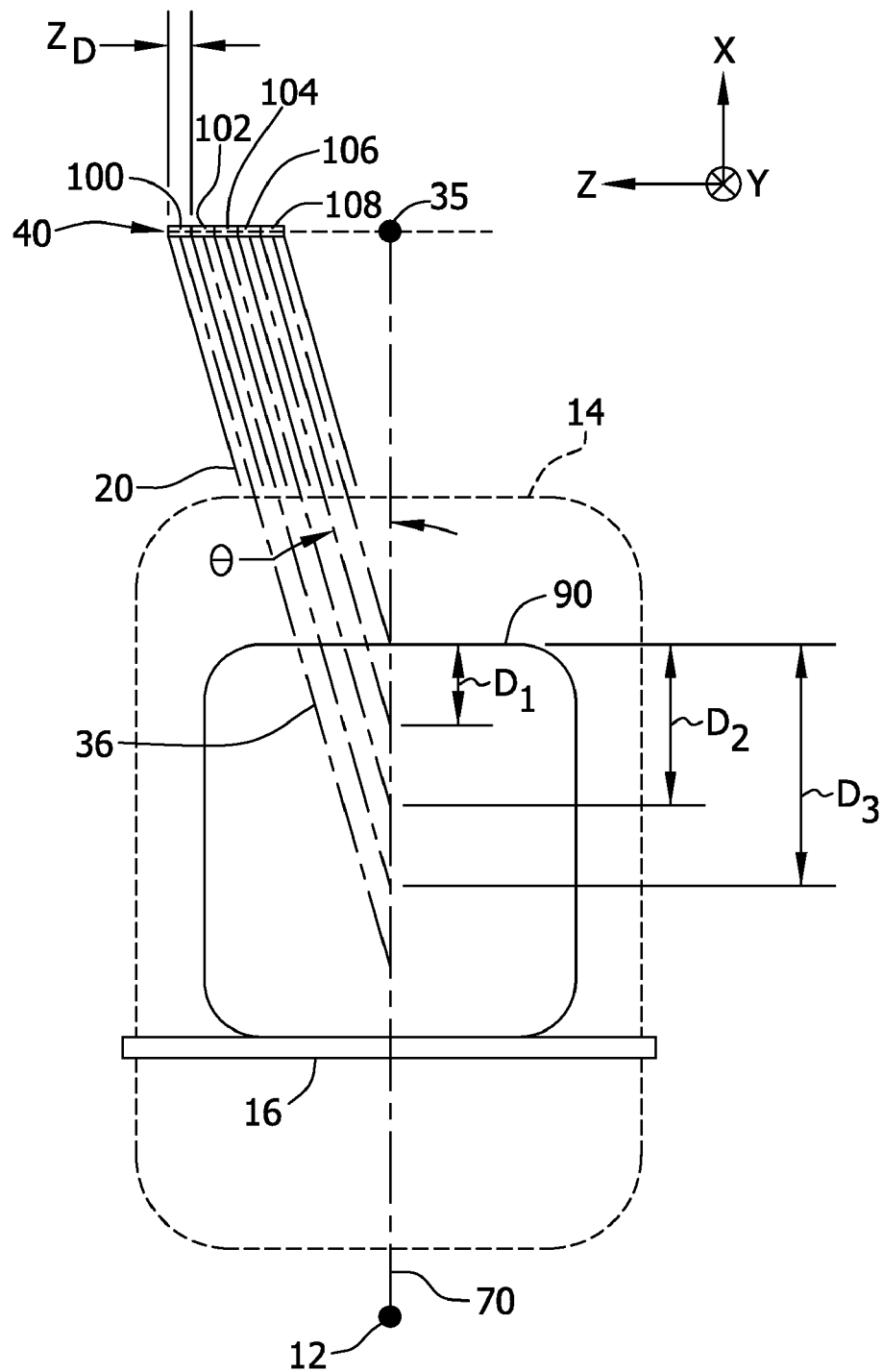

FIG. 3 is a schematic view, in an X-Z plane, of an exemplary embodiment an X-ray scatter detection system embodied within security detection system 10. In particular, FIG. 3 illustrates one of the plurality 24 of scatter detectors and scattered radiation 36 it receives from one of the set 34 of X-ray pencil beams in the exemplary embodiment. Scatter detector 40 and pencil beam 70, as shown in FIGS. 2 and 3, are used as a representative example. Scatter detector 40 includes a plurality of detector strips placed sequentially adjacent along a direction substantially parallel to the Z-axis. In an exemplary embodiment, the plurality of detector strips includes eighteen detector strips. In the embodiment shown in FIG. 3, for the sake of clarity, only five detector strips 100, 102, 104, 106 and 108 are shown. In alternative embodiments, any suitable number of detector strips along a direction substantially parallel to the Z-axis may be used.

Each detector strip 100, 102, 104, 106 and 108 has an associated width b measured in a direction substantially parallel to the Y-axis (not visible in FIG. 3) and an associated height $Z_D$ measured in a direction substantially parallel to the Z-axis. In certain embodiments, each detector strip 100, 102, 104, 106 and 108 is a one-dimensional or two-dimensional pixellated detector array with a composite active width b measured in a direction substantially parallel to the Y-axis (not visible in FIG. 3) and a composite active height $Z_D$ measured in a direction substantially parallel to the Z-axis.

With reference to FIGS. 1, 2 and 3, secondary collimator 20 is configured to facilitate ensuring that the portion of scattered radiation 36 arriving at scatter detector 40 has a constant scatter angle θ with respect to X-ray pencil beam 70. Furthermore, secondary collimator 20 is configured to facilitate determining the depth, measured in a direction substantially parallel to the X-axis, at which the portion of scattered radiation 36 received at each detector strip 100, 102, 104, 106 and 108 originated in a container 90 under examination. For example, because secondary collimator 20 absorbs (i.e., does not transmit to scatter detector 40) scattered radiation not parallel to scattered radiation 36, it can be determined that a portion of scattered radiation 36 received at detector strip 100 originated from an impingement of X-ray pencil beam 70 at approximately a first side or a bottom of container 90, a portion of scattered radiation 36 received at detector strip 102 originated from an impingement of X-ray pencil beam 70 at approximately a depth $D_3$ in container 90, a portion of scattered radiation 36 received at detector strip 104 originated from an impingement of X-ray pencil beam 70 at approximately a depth $D_2$ in container 90, a portion of scattered radiation 36 received at detector strip 106 originated from an impingement of X-ray pencil beam 70 at approximately a depth $D_1$ in container 90, and a portion of scattered radiation 36 received at detector strip 108 originated from an impingement of X-ray pencil beam 70 at approximately an opposing second side or top of container 90.

Figure 4:
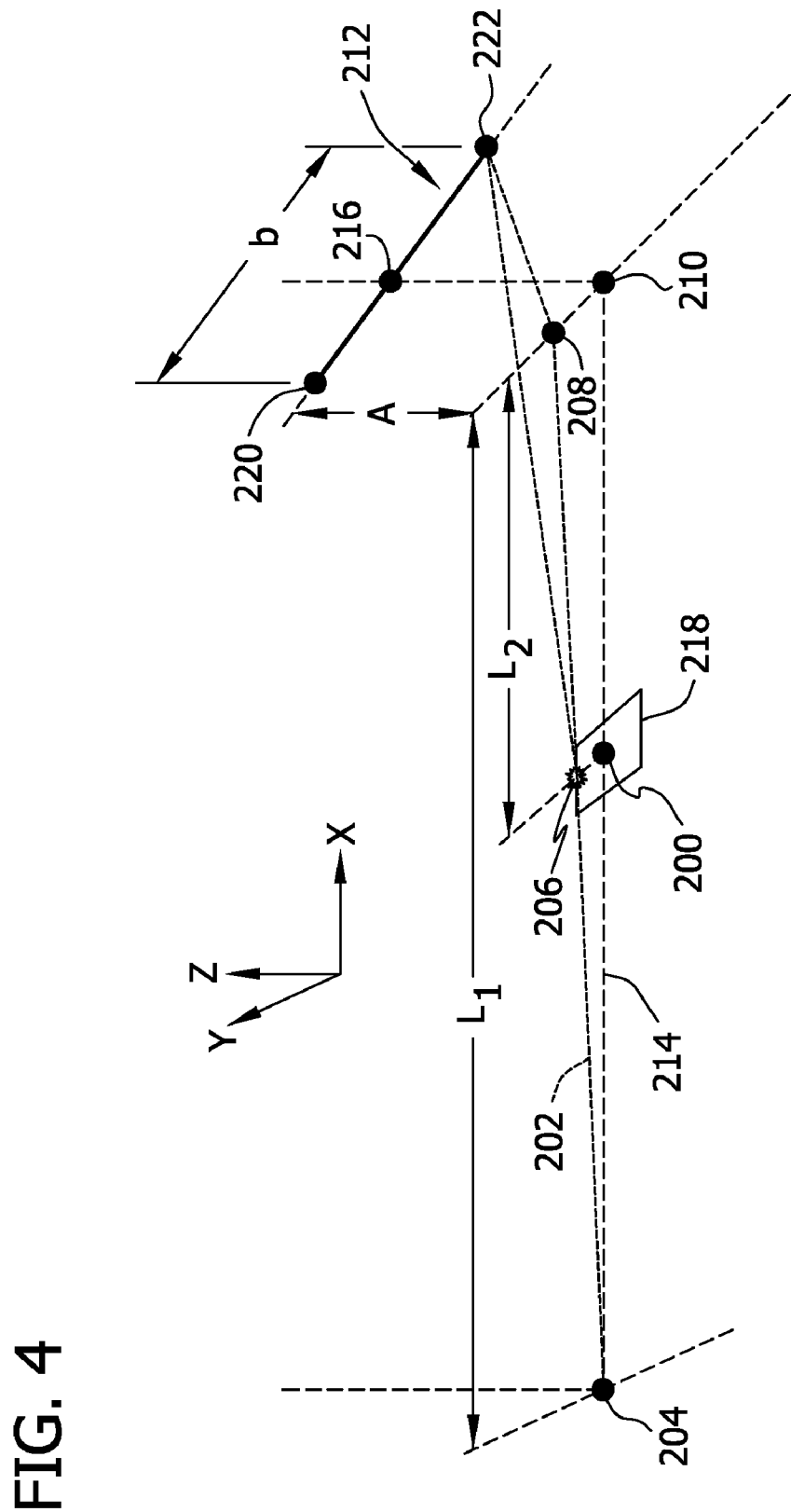

FIG. 4 illustrates an angular broadening $\Delta\theta$ of the scatter angle $\theta$ for a representative object voxel 218 centered at a point 200. A focus point 204 of X-ray source 12 emits a pencil beam centered on line 214 and directed at a target point 210. A line 202 is drawn from focus point 204 to subtend, in an X-Y plane in which line 214 lies, an edge point 206 of object voxel 218 under examination. Line 202 represents an outer extent or edge, in the X-Y plane in which line 214 lies, of the pencil beam centered on line 214. A distance between points 204 and 210 is $L_1$, while a distance between point 200 and point 210 is $L_2$.

A first scatter detector strip 212 is centered on point 216, extends to a first width b between point 220 and point 222 in a direction substantially parallel to the Y-axis, and has an infinitesimal height along a direction substantially parallel to the Z-axis. First detector strip 212 is separated from the X-Y plane in which lines 202 and 214 lie by a distance A measured in a direction substantially parallel to the Z-axis. Line 202 intersects a Y-Z plane in which first detector strip 212 lies at a point 208. The angle $\angle 216\text{-}200\text{-}210$ defines the scatter angle $\theta$ of scattered radiation received by first detector strip 212. In addition, first detector strip 212 receives radiation at a skew scatter angle, $\theta'$, defined by the angle $\angle 208\text{-}206\text{-}222$. The angular broadening $\Delta\theta$ is defined as $\theta'$ less $\theta$.

For the case that the energy resolution of the scatter detector is high enough, the angular broadening $\Delta\theta$ is related to the widths $\Delta x$ of the measured X-ray diffraction Bragg peaks by the following equation, where x is the momentum transfer from an X-ray photon to the material in object voxel 200:

$$\frac{\Delta x}{x} = \frac{\Delta\theta}{\theta} \tag{1}$$

It is a requirement on the one hand for an increased material detection rate that the XDI profile should have narrow widths $\Delta x$, which implies from Equation 1 that the angular broadening, $\Delta\theta$, should be low. In tension with this requirement, a low false alarm rate requires an increased number of photons to be accumulated in the XDI profile. To maximize the number of photons received at first detector strip 212, sometimes termed "detector acceptance" or "photon throughput," for object voxel 218 under investigation, the product of the solid angle that the voxel subtends at focus point 204 and the solid angle that first detector strip 212 subtends at the voxel should be maximized. The angle $\angle 208\text{-}204\text{-}210$ provides a measure for the source solid angle, and the angle $\angle 216\text{-}206\text{-}222$ provides a measure for the detector solid angle. For a given angular broadening, $\Delta\theta$, the solid angle product maximization condition is satisfied when:

$$\frac{\angle 208\text{-}204\text{-}210}{\angle 216\text{-}206\text{-}222} = \frac{L_2}{L_1} \tag{2}$$

Figure 5:
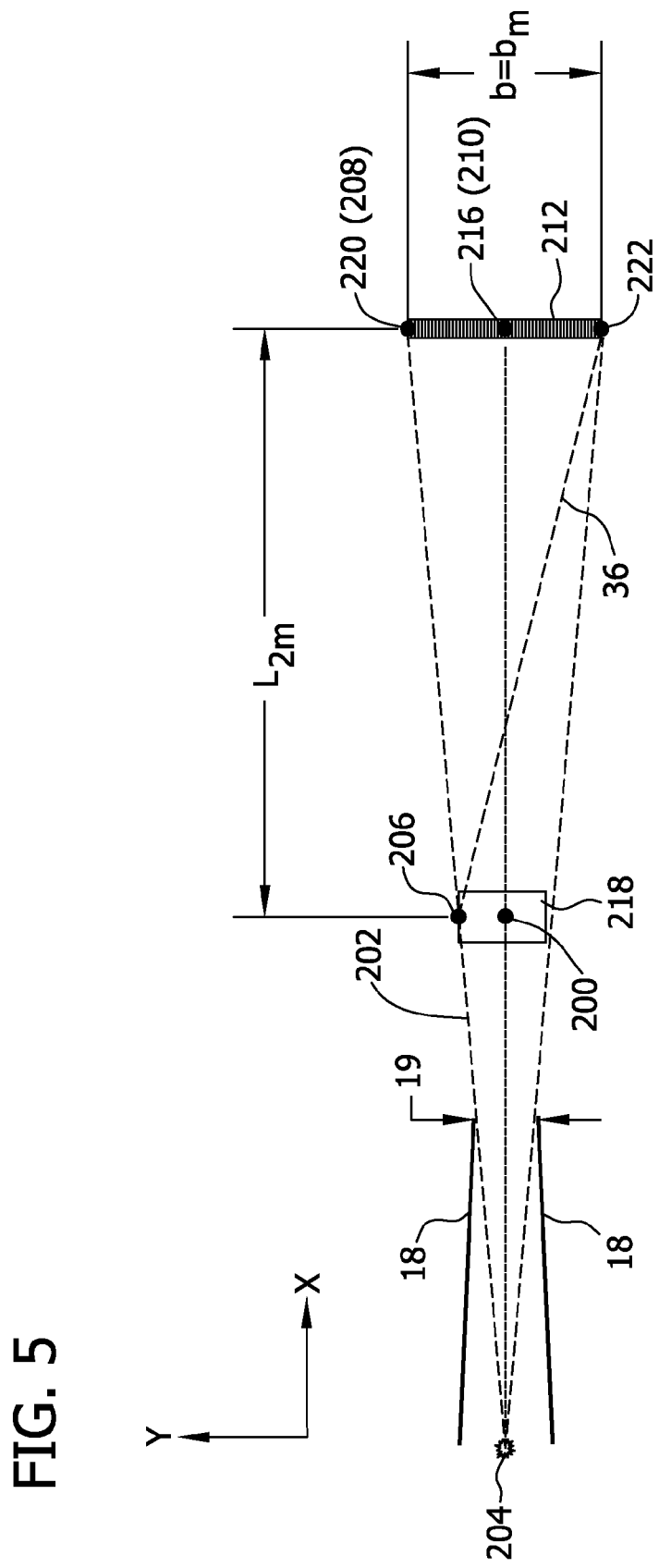

FIG. 5 shows an X-Y plane projection of the optimal geometric relationship for first detector strip 212 as established by Equation (2). With reference to FIGS. 1, 3, 4 and 5, first detector strip 212 is separated in the Z-direction from the X-Y plane in which points 200, 204, 206, 208 and 210 lie. The angle $\angle 208\text{-}204\text{-}210$ is determined by a known channel width 19 of primary collimator 18, and the X-direction component of distances $L_1$, from the source focus point 204 to first detector strip 212, and $L_2$, from the point 200 or center of object voxel 218 to first detector strip 212, are also known. The remaining element of Equation (2), angle $\angle 216\text{-}206\text{-}222$, is dependent upon the active first width b in the Y-direction of first detector strip 212. To satisfy Equation (2), the first width b of detector strip 212 is chosen to equal the linear extent in the Y-direction of pencil beam 202 at the Y-Z plane in which detector strip 212 lies. In other words, with reference also to FIG. 4, first width b is chosen so that point 208 shares a Y-coordinate with point 220. Therefore, in certain embodiments of the invention, first detector strip 212 has a first width b equal to a linear extent of the X-ray pencil beam 202 measured at the Y-Z plane in which the first detector strip 212 lies, and measured in a direction parallel to the first width b. As a result, for a given angular broadening, $\Delta\theta$, the product of the solid angle that voxel 218 subtends at focus point 204 and the solid angle that detector strip 212 subtends at voxel 218, and hence the photon throughput, is maximized for detector strip 212 in the exemplary embodiment. This optimum detector width b for detector strip 212 as found from Equation (2) for a given angular broadening $\Delta\theta$ may be labeled $b_m$, and the distance $L_2$ from the Y-Z plane in which detector strip 212 lies to object voxel 218 from which detector strip 212 receives scattered radiation 36 may be labeled $L_{2m}$.

In the exemplary embodiment, Equation (2) is satisfied for detector strip 104, which lies at the center of representative scatter detector 40 of the exemplary embodiment as shown in FIG. 3. As is shown in FIG. 3, detector strip 104 receives scattered radiation 36 originating from approximately a center portion of container 90. In alternative embodiments, Equation (2) is satisfied for a different one of the detector strips of scatter detector 40.

Moreover, in the exemplary embodiment, the active widths b in the Y-direction of the other detector strips 100, 102, 106 and 108 are chosen to preserve the given angular broadening, $\Delta\theta$, for which the photon throughput to detector strip 104 was optimized. As previously described and as shown in FIG. 3, each detector strip 100, 102, 104, 106 and 108 receives a portion of scattered radiation 36 originating from a different known depth, measured in a direction substantially parallel to the X-axis, within container 90. Returning to FIGS. 3, 4 and 5, the skew scatter angle, $\theta'$, defined by the angle $\angle 208\text{-}206\text{-}222$, may be approximated as the angle $\angle 210\text{-}200\text{-}222$. In turn, angle $\angle 210\text{-}200\text{-}222$ may be approximated for each detector strip 100, 102, 104, 106 and 108 as follows:

$$\angle 210\text{-}200\text{-}222 \cong \frac{\sqrt{(b/2)^2 + (L_2\tan(\theta))^2}}{L_2} \tag{3}$$

Equation (3) demonstrates that the skew scatter angle $\theta'$, and thus the angular broadening, $\Delta\theta$, varies with the separation $L_2$ of object voxel 218 from detector strip 212 in the X-direction. Therefore, for a detector strip 100, 102, 106 or 108 that receives a portion of scattered radiation 36 originating from any known depth $L_2$ measured in a direction substantially parallel to the X-axis, the optimum detector strip width b that preserves the given angular broadening $\Delta\theta$ is given by the equation:

$$b = b_m \frac{L_2}{L_{2m}} \quad (4)$$

Similarly, the optimum height, $Z_D$, measured in a direction substantially parallel to the Z-axis, for each detector strip 100, 102, 104, 106 and 108 may be derived to be the constant value given by the equation:

$$Z_D = \frac{b_m^2}{8L_{2m}\tan(\theta)} \quad (5)$$

Figure 6:
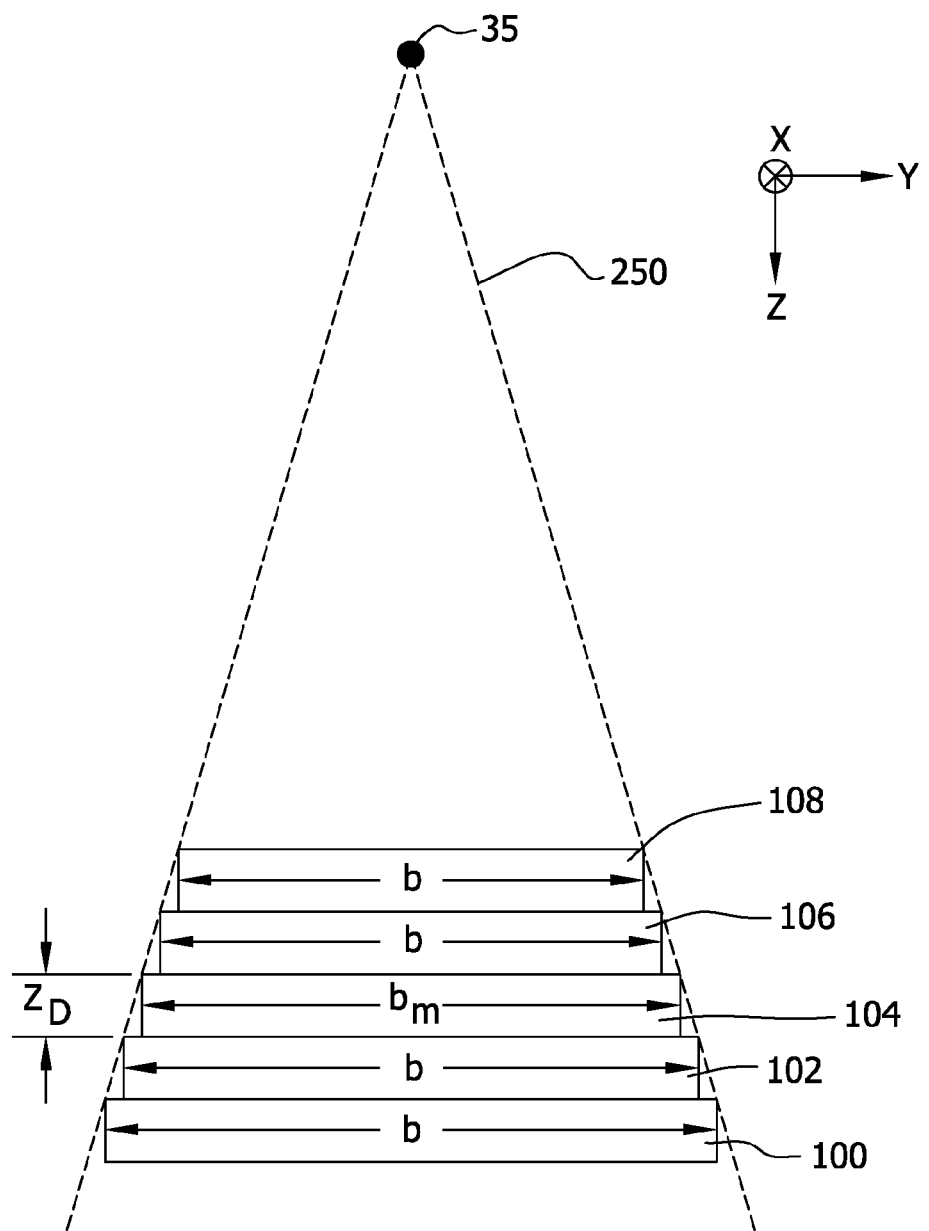

FIG. 6 is a schematic view, in a Y-Z plane as seen from X-ray source 12, of the geometry of scatter detector 40 according to the exemplary embodiment. With reference to FIGS. 3, 4, 5 and 6, detector strip 104 has optimal width $b_m$, as measured in a direction substantially parallel to the Y-axis, chosen to satisfy Equation (2). Each other detector strip 100, 102, 106 and 108 has a respective width b determined from Equation (4), dependent upon the relative depth in container 90 from which it receives scattered radiation 36. Moreover, each detector strip 100, 102, 104, 106 and 108 has height $Z_D$, as measured in a direction substantially parallel to the Z-axis, chosen according to Equation (5). As is shown in FIG. 6, detector strips 100, 102, 104, 106 and 108 lie within a substantially triangular outline 250 with a vertex at target point 35 of pencil beam 70 (both shown in FIG. 3). Detector strip 108 with the shortest width b receives scattered radiation 36 from near the top of examination area 14, while detector strip 100 with the longest width b receives scattered radiation 36 from near the bottom of examination area 14 (as shown in FIG. 3).

In certain embodiments, scatter detectors 42 and 44 also have the geometry of FIG. 6. In alternative embodiments, any one of scatter detectors 40, 42 and 44 have the geometry shown in FIG. 6, and the remaining scatter detectors have different geometries. In further alternative embodiments, any suitable number of scatter detectors are used, and one or more of them have the geometry of FIG. 6.

Figure 7:
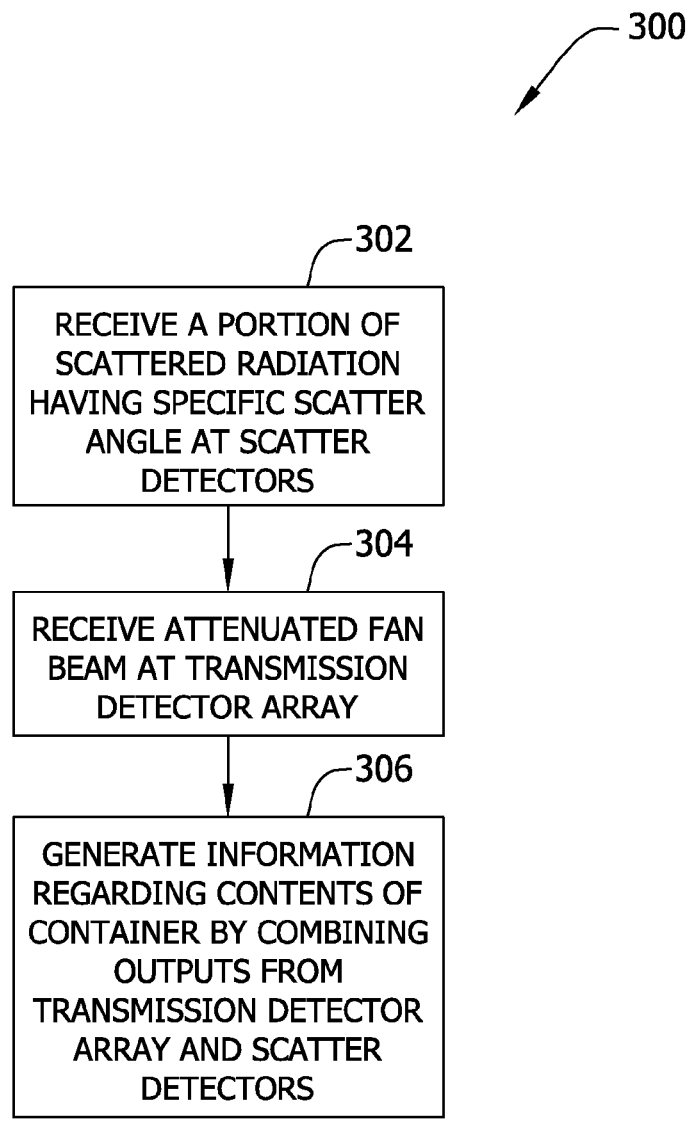

FIG. 7 is a flowchart representing an exemplary method 300 of operating security detection system 10. Unless otherwise indicated, one or more of the steps included in FIG. 7 may be performed sequentially, concurrently, or in any suitable order. With reference to FIGS. 3, 6 and 7, in the exemplary method, the plurality 24 of scatter detectors receives 302 a portion of scattered radiation 36 having scatter angle $\theta$. In certain embodiments, at least one of the plurality 24 of scatter detectors is located substantially in a Y-Z plane as shown in FIG. 4, and includes a plurality of detector strips, such as detector strips 100, 102, 104, 106 and 108. Moreover, the first width $b_m$ of a first detector strip, such as detector strip 104, is selected during manufacture or refitting such that Equation (2) is satisfied. In other words, the first width $b_m$ of the first detector strip, such as detector strip 104, is equal to a linear extent of an X-ray pencil beam from the set 34 of X-ray pencil beams measured at the Y-Z plane in a direction parallel to the first width $b_m$. In addition, transmission detector array 22 receives 304 fan beam 32 attenuated by the container 90. Data processing system 112 generates 306 information regarding the contents of container 90 by combining an output from transmission detector array 22 and an output from the plurality 24 of scatter detectors.

In certain embodiments of exemplary method 300, the portion of the scattered radiation 36 comprises a plurality of portions of scattered radiation 36 as shown in FIG. 3. The step of receiving 302 a portion of scattered radiation 36 having scatter angle $\theta$ includes the first detector strip, such as detector strip 104, receiving a first portion of a plurality of portions of scattered radiation 36, and a second detector strip, such as detector strip 100, 102, 106 or 108, receiving a second portion of the plurality of portions of scattered radiation 36. The width b of the second detector strip is selected during manufacture or refitting to satisfy Equation (4), and the height $Z_D$ of at least one of the detector strips, such as detector strip 100, 102, 104, 106 or 108, is selected during manufacture or refitting to satisfy Equation (5).

The above-described embodiments facilitate combining the advantages of multiview transmission imaging and XDI using the same X-ray source in a single security detection system, decreasing a need to implement separate AT and XDI scanning systems. More specifically, the above-described embodiments decrease both a size and a cost of the security detection system, and also decrease a time needed to complete an investigation of each container. The above-described embodiments also facilitate decreasing an angular broadening of a scatter angle associated with the detector, therefore facilitating an X-ray diffraction profile with decreased measured peak widths of momentum transfer, which in turn facilitates an increase in a material detection rate. Moreover, the above-described embodiments facilitate maximizing a number of photons received at each scatter detector for a given constant angular broadening, which in turn facilitates a decrease in a false positive detection rate. Therefore, the above-described embodiments facilitate, for example, an identification of liquids within glass bottles, metal cans, thermos flasks, or other devices concealed in suitcases without the need to remove the device from the suitcase.

In addition, the above-described embodiments facilitate improved AT functionality, by virtue of the container being imaged from many, for example forty or one hundred, projection directions. The above-described embodiments also facilitate identification of conventional crystalline explosives as well as liquid, amorphous and homemade explosives by virtue of x-ray diffraction imaging of the container using a small number, for example three, of coherent scatter detectors in an inverse geometry for full container coverage.

Exemplary embodiments of an X-ray diffraction imaging system, including an X-ray scatter detection system, and a method for operating an X-ray diffraction imaging system are described above in detail. The X-ray diffraction imaging system, X-ray scatter detection system and method are not limited to the specific embodiments described herein. For example, the X-ray scatter detection system also may be used in combination with other inspection/detection systems and/or inspection methods, and is not limited to practice with only the security detection system as described herein. Moreover, the X-ray diffraction imaging system, X-ray scatter detection system and method for operating an X-ray diffraction imaging system described herein have applications beyond security detection including applications in the plastics recycling, pharmaceutical and non-destructive testing industries.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An X-ray diffraction imaging system, comprising:
an X-ray source configured to emit an X-ray fan beam and a set of X-ray pencil beams;
an examination area;
a plurality of scatter detectors, each of said plurality of scatter detectors configured to receive scattered radiation from an interaction of an X-ray pencil beam of the set of X-ray pencil beams and a container in said examination area, the scattered radiation having a scatter angle, wherein at least one of said plurality of scatter detectors is located substantially in a plane, said at least one scatter detector comprises a plurality of detector strips, a first detector strip of said plurality of detector strips having a first width equal to a width of the X-ray pencil beam measured where the X-ray pencil beam crosses the plane;
a transmission detector array configured to receive the X-ray fan beam attenuated by the container; and
a data processing system configured to combine an output from said transmission detector array and an output from said plurality of scatter detectors to generate information regarding the container.

2. An X-ray diffraction imaging system in accordance with claim 1, wherein:
the scattered radiation comprises a plurality of portions of scattered radiation;
said first detector strip is configured to receive a first portion of the plurality of portions of scattered radiation, the first portion originating from a first distance, measured perpendicular to the plane, from the plane; and
a second detector strip of said plurality of detector strips is configured to receive a second portion of the plurality of portions of scattered radiation, the second portion originating from a second distance, measured perpendicular to the plane, from the plane, and said second detector strip has a second width b defined by:

$$b = b_m \frac{L_2}{L_{2m}}$$

wherein $b_m$ is the first width, $L_{2m}$ is the first distance, and $L_2$ is the second distance.

3. An X-ray diffraction imaging system in accordance with claim 1, wherein:
the scattered radiation comprises a plurality of portions of scattered radiation;
said first detector strip is configured to receive a first portion of the plurality of portions of scattered radiation, the first portion originating from a first distance, measured perpendicular to the plane, from the plane; and
at least one of said plurality of detector strips comprises a height $Z_D$ defined by:

$$Z_D = \frac{b_m^2}{8 L_{2m} \tan(\theta)}$$

wherein $b_m$ is the first width, $L_{2m}$ is the first distance, and $\theta$ is the scatter angle.

4. An X-ray diffraction imaging system in accordance with claim 1, wherein said X-ray source is configured to emit the set of X-ray pencil beams substantially in a first plane and the X-ray fan beam substantially in a second plane.

5. An X-ray diffraction imaging system in accordance with claim 1, wherein said data processing system is further configured to perform an X-ray diffraction analysis using the output from said plurality of scatter detectors, and the information regarding the container comprises one of a multiview projection and a section image of the container, the one of a multiview projection and a section image identifies a location in the container of a material detected by the X-ray diffraction analysis.

6. An X-ray diffraction imaging system in accordance with claim 1, wherein said X-ray source comprises a plurality of focus points, each of said plurality of focus points is configured to emit the X-ray fan beam and the set of X-ray pencil beams.

7. An X-ray diffraction imaging system in accordance with claim 6, wherein said plurality of focus points are located substantially along an axis of said X-ray source, said X-ray source is configured to generate the X-ray fan beam and the set of X-ray pencil beams from each focus point of said plurality of focus points in sequence along the axis.

8. A method of operating an X-ray diffraction imaging system, said method comprising:
receiving at a plurality of scatter detectors a portion of scattered radiation from a container, the scattered radiation having a scatter angle, wherein at least one of the plurality of scatter detectors is located substantially in a plane, the at least one scatter detector comprises a plurality of detector strips, and a first width of a first detector strip of the plurality of detector strips is equal to a width of an X-ray pencil beam measured where the X-ray pencil beam crosses the plane;
receiving an X-ray fan beam attenuated by the container at a transmission detector array; and
generating information regarding the contents of the container by combining an output from the transmission detector array and an output from the plurality of scatter detectors.

9. A method in accordance with claim 8, wherein the portion of the scattered radiation comprises a plurality of portions of scattered radiation, said receiving at a plurality of scatter detectors a portion of scattered radiation further comprises:
receiving a first portion of the plurality of portions of scattered radiation at the first detector strip of the plurality of detector strips, the first portion originating from a first distance, measured perpendicular to the plane, from the plane; and
receiving a second portion of the plurality of portions of scattered radiation at a second detector strip of the plurality of detector strips, the second portion originating from a second distance, measured perpendicular to the plane, from the plane, wherein a second width b of the second detector strip is defined by:

$$b = b_m \frac{L_2}{L_{2m}}$$

wherein $b_m$ is the first width, $L_{2m}$ is the first distance, and $L_2$ is the second distance.

10. A method in accordance with claim 8, wherein the portion of the scattered radiation comprises a plurality of portions of scattered radiation, said receiving at a plurality of scatter detectors a portion of scattered radiation further comprises receiving a first portion of the plurality of portions of scattered radiation at the first detector strip of the plurality of detector strips, the first portion originating from a first distance, measured perpendicular to the plane, from the plane, wherein a height $Z_D$ of at least one of the plurality of detector strips is defined by:

$$Z_D = \frac{b_m^2}{8 L_{2m} \tan(\theta)}$$

wherein $b_m$ is the first width, $L_{2m}$ is the first distance, and $\theta$ is the scatter angle.

11. A method in accordance with claim 8, wherein the scattered radiation arises from a set of X-ray pencil beams directed at the container, the set of X-ray pencil beams lies substantially in a first plane, said method further comprises orienting the X-ray fan beam substantially in a second plane.

12. A method in accordance with claim 8, wherein said generating information regarding the contents of the container further comprises:
performing an X-ray diffraction analysis using the output from the plurality of scatter detectors; and
generating one of a multiview projection and a section image of the container, the one of a multiview projection and a section image identifies a location in the container of a material detected by the X-ray diffraction analysis.

13. A method in accordance with claim 8, wherein the scattered radiation arises from a set of X-ray pencil beams directed at the container, said method further comprises transmitting the X-ray fan beam and the set of X-ray pencil beams from each of a plurality of focus points of an X-ray source.

14. A method in accordance with claim 13, wherein the plurality of focus points are located substantially along an axis of the X-ray source, said transmitting the X-ray fan beam and the set of X-ray pencil beams from each of the plurality of focus points further comprises generating the X-ray fan beam and the set of X-ray pencil beams from each focus point of the plurality of focus points in sequence along the axis.

15. An X-ray scatter detection system, comprising:
an X-ray source configured to emit an X-ray pencil beam; and
a scatter detector configured to receive scattered radiation having a scatter angle from the X-ray pencil beam, said scatter detector located substantially in a plane, said scatter detector comprising a plurality of detector strips, a first detector strip of said plurality of detector strips having a first width equal to a width of the X-ray pencil beam measured where the X-ray pencil beam crosses the plane.

16. An X-ray scatter detection system in accordance with claim 15, wherein:
the scattered radiation comprises a plurality of portions of scattered radiation;
said first detector strip is configured to receive a first portion of the plurality of portions of scattered radiation, the first portion originating from a first distance, measured perpendicular to the plane, from the plane; and
a second detector strip of said plurality of detector strips is configured to receive a second portion of the plurality of portions of scattered radiation, the second portion originating from a second distance, measured perpendicular to the plane, from the plane, said second detector strip comprises a second width b defined by:

$$b = b_m \frac{L_2}{L_{2m}}$$

wherein $b_m$ is the first width, $L_{2m}$ is the first distance, and $L_2$ is the second distance.

17. An X-ray scatter detection system in accordance with claim 15, wherein:
the scattered radiation comprises a plurality of portions of scattered radiation;
said first detector strip is configured to receive a first portion of the plurality of portions of scattered radiation, the first portion originating from a first distance, measured perpendicular to the plane, from the plane; and
at least one of said plurality of detector strips comprises a height $Z_D$ defined by:

$$Z_D = \frac{b_m^2}{8 L_{2m} \tan(\theta)}$$

wherein $b_m$ is the first width, $L_{2m}$ is the first distance, and $\theta$ is the scatter angle.

18. An X-ray scatter detection system in accordance with claim 15, further comprising a primary collimator, wherein the width of the X-ray pencil beam measured at the plane is determined by a channel width of the primary collimator.

* * * * *